United States Patent
Hsiao et al.

(10) Patent No.: US 9,916,418 B2
(45) Date of Patent: Mar. 13, 2018

(54) UPLOADING MEASUREMENT DATA OF NON-CONNECTED MEDICAL MEASURING DEVICES

(71) Applicant: International Business Machines Corporation, Armonk, NY (US)

(72) Inventors: Jen-Hao Hsiao, Taipei (TW); Ci-Wei Lan, Keelung (TW); Ya-Fan Yeh, Taipei (TW)

(73) Assignee: INTERNATIONAL BUSINESS MACHINES CORPORATION, Armonky, NY (US)

( * ) Notice: Subject to any disclaimer, the term of this patent is extended or adjusted under 35 U.S.C. 154(b) by 555 days.

(21) Appl. No.: 13/894,862

(22) Filed: May 15, 2013

(65) Prior Publication Data
US 2013/0325506 A1    Dec. 5, 2013

(30) Foreign Application Priority Data
May 31, 2012  (TW) .............................. 101119680 A

(51) Int. Cl.
G06F 19/00      (2018.01)

(52) U.S. Cl.
CPC .......... *G06F 19/321* (2013.01); *G06F 19/322* (2013.01)

(58) Field of Classification Search
CPC .......................... A61B 5/0022; G06F 19/3406
USPC ..... 600/300, 365; 705/2, 3, 19; 706/2, 3, 19
See application file for complete search history.

(56) References Cited

U.S. PATENT DOCUMENTS

| | | | |
|---|---|---|---|
| 6,148,298 A * | 11/2000 | LaStrange et al. | |
| 6,264,614 B1 | 7/2001 | Albert et al. | |
| 6,406,434 B2 * | 6/2002 | Inukai ................. | A61B 5/0225 600/490 |
| 7,206,630 B1 | 4/2007 | Tarler | |
| 7,395,117 B2 | 7/2008 | Mazar et al. | |
| 7,475,020 B2 | 1/2009 | Hasan et al. | |
| 7,555,437 B2 * | 6/2009 | Pierce ................. | G06F 19/321 705/2 |

(Continued)

OTHER PUBLICATIONS

Benson et al, "Intelligent Data Management for Wireless Medical Devices", Mddical Device and Diagnostic Industry; Feb. 8, 2003, 4 pages. http://www.mddionline.com/article/intelligent-data-wireless-devices.

(Continued)

*Primary Examiner* — Minnah Seoh
*Assistant Examiner* — Teresa Williams
(74) *Attorney, Agent, or Firm* — Cantor Colburn LLP; Bryan Butler

(57) ABSTRACT

Embodiments are directed to detecting and uploading measurement data of a non-connected medical measuring device. Embodiments include capturing an image of an identification object and a beginning event image of a medical measuring device and extracting identification data from the image of the identification object. Based on detecting that the identification object has been removed, an ending event image of the medical measuring device is captured. Embodiments include determining if a measurement event has occurred by comparing the ending event image and the beginning event image. Based on determining that the measurement event occurred, a measurement data of the ending event image is extracted and upload to a personal health record database.

12 Claims, 4 Drawing Sheets

(56) References Cited

U.S. PATENT DOCUMENTS

| | | | | |
|---|---|---|---|---|
| 7,823,773 | B2* | 11/2010 | Hatzav et al. | 235/380 |
| 8,103,665 | B2* | 1/2012 | Abbott et al. | 707/729 |
| 8,315,681 | B2* | 11/2012 | Kanayama et al. | 600/316 |
| 2003/0069752 | A1* | 4/2003 | LeDain | G06F 19/3418 705/2 |
| 2003/0158891 | A1 | 8/2003 | Lei et al. | |
| 2004/0034603 | A1* | 2/2004 | Hastings et al. | 705/63 |
| 2005/0075907 | A1* | 4/2005 | Rao | A61B 5/0002 705/2 |
| 2006/0142648 | A1 | 1/2006 | Banet et al. | |
| 2006/0111620 | A1* | 5/2006 | Squilla | A61B 5/00 600/300 |
| 2007/0181664 | A1* | 8/2007 | Hatzav et al. | 235/375 |
| 2008/0021730 | A1 | 1/2008 | Holla et al. | |
| 2008/0119710 | A1* | 5/2008 | Reggiardo et al. | 600/365 |
| 2008/0124694 | A1* | 5/2008 | Miller | G09B 5/00 434/262 |
| 2009/0138207 | A1* | 5/2009 | Cosentino et al. | 702/19 |
| 2009/0143652 | A1* | 6/2009 | Warburton | G06F 19/3418 600/301 |
| 2009/0216142 | A1* | 8/2009 | Stelzer | A61B 5/04085 600/509 |
| 2009/0240524 | A1* | 9/2009 | Bluth | A61B 5/02055 705/2 |
| 2010/0069732 | A1* | 3/2010 | Reggiardo et al. | 600/365 |
| 2010/0087167 | A1 | 4/2010 | Tsurutome et al. | |
| 2010/0245553 | A1 | 9/2010 | Schuler et al. | |
| 2010/0317953 | A1* | 12/2010 | Reggiardo et al. | 600/365 |
| 2011/0092825 | A1* | 4/2011 | Gopinathan | A61B 5/411 600/483 |
| 2011/0122995 | A1* | 5/2011 | Ferro, Jr. | A61B 6/4429 378/62 |
| 2011/0213621 | A1 | 9/2011 | Dicks et al. | |

OTHER PUBLICATIONS

Jovanov et al, "Patient Monitoring Using Personal Area Networks of Wireless Intelligent Sensors," Proceedings of 2000 IEEE EMBS International Conference on Information Technology Applications in Biomedicine; Nov. 9, 2000; pp. 22-27.

* cited by examiner

UPLOADING MEASUREMENT DATA OF NON-CONNECTED MEDICAL MEASURING DEVICES

This application claims the benefit of, and priority to, Taiwanese Patent Application 101119680, filed on May, 31, 2012.

BACKGROUND

The present disclosure relates generally to collecting data from medical devices, and more specifically, to automatically detecting and uploading measurement data of a non-connected medical measuring device.

Due to the prevalence of data networks, people can collect data easily and upload the data to a cloud-enabled storage device through a network, such as a cellular data network, a Wi-Fi hotspot, or the like. From a medical perspective, medical data are always collected by means of a medical measuring device, such as a body weight meter, a sphygmomanometer, or an electrocardiograph. Currently, medical devices collect and store data manually and data is transferred from the medical devices via an additional output port (such as USB). Also, it is feasible for medical data to be collected by means of a built-in wireless module. Most conventional medical measuring devices are not only non-connected to data networks, but also incapable of being connected to the data networks.

BRIEF SUMMARY

Embodiments include systems, computer programs, and methods of detecting and uploading measurement data of a non-connected medical measuring device. Embodiments include capturing an image of an identification object and a beginning event image of a medical measuring device and extracting identification data from the image of the identification object. Based on detecting that the identification object has been removed, an ending event image of the medical measuring device is captured. Embodiments include determining if a measurement event has occurred by comparing the ending event image and the beginning event image. Based on determining that the measurement event occurred, a measurement data of the ending event image is extracted and upload to a personal health record database.

Additional features and advantages are realized through the techniques of the present disclosure. Other embodiments and aspects of the disclosure are described in detail herein. For a better understanding of the disclosure with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The foregoing and other features, and advantages of the disclosure are apparent from the following detailed description taken in conjunction with the accompanying drawings in which:

DETAILED DESCRIPTION

Figure 1:
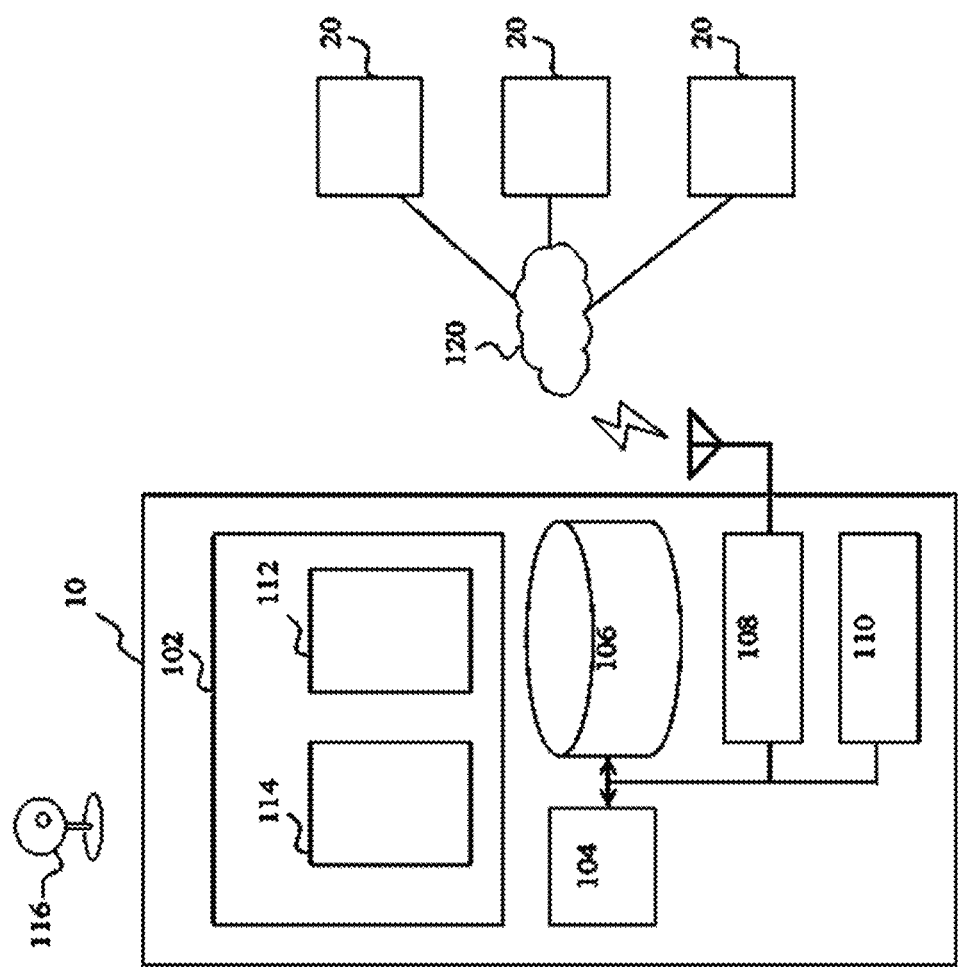
FIG. 1 is a block diagram of a computer device according to an exemplary embodiment.

Referring now to FIG. 1, a block diagram of a computer device 10 in accordance with an exemplary embodiment is shown. The computer device 10 includes a display screen 102, a digital video camcorder 116, a processor 104, a memory 106, a communication module 108, and a data input module 110. In exemplary embodiments, the computer device 10 may be implemented in the form of a conventional notebook computer or another suit portable information device such as a mobile phone or a smartphone device.

In exemplary embodiments, the processor 104 of the computing device 10 is a central processor and the memory 106 is a flash memory for storing applications and data, which can be accessed and executed by the processor 104. In exemplary embodiments, the communication module 108 is capable of connecting the computing device 10 to a network 120. The communication module 108 may be configured to utilize UMTS, CDMA, LTE, GSM, Wi-Fi, or another suitable communications protocol to connect to one or more servers 20 via a network 120. In exemplary embodiments, the data input module 110 and the display screen 102 may be combined as a touch screen for user to create data or input instructions. In exemplary embodiments, the digital video camcorder 116 is a camcorder or cameral built into the computer device 10 or connected to the computer device 10 via an input port of the computer device 10.

In another embodiment, the computer device 10 may be a mainframe or a high-level workstation with robust processing capacity and storing capacity and provides a webpage interface whereby the user accesses the computer device 10 via a network by means of a computer device or portable device in wide use.

The network can be any type of know network, including, but not limited to, a wide area network (WAN), a local area network (LAN), or a connection to the Internet through an Internet service provider (ISP). In addition, the network connection may be a wired or a wireless connection. Persons skilled in the art are able to understand that the network can also have other hardware and software elements (such as an additional computer system, a router, or a firewall) not shown in the accompanying drawings.

Figure 2:
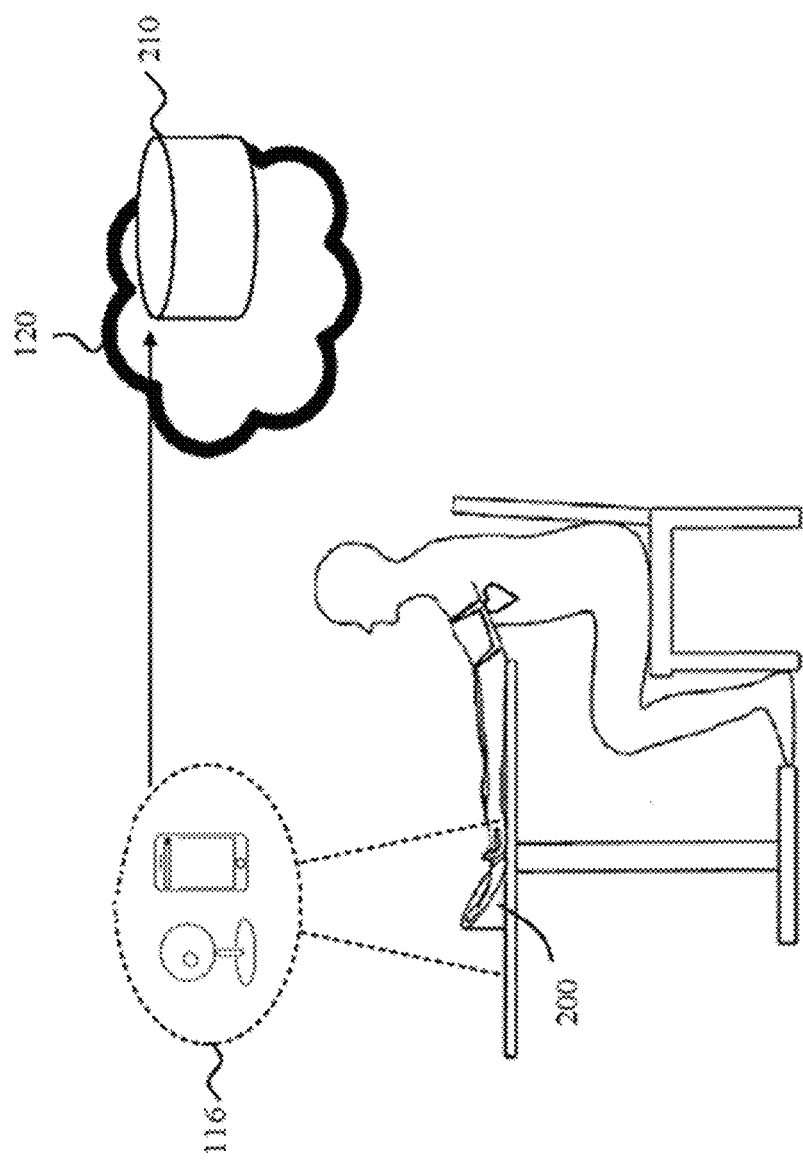
FIG. 2 is a schematic view of an application scenario according to an exemplary embodiment.

Referring now to FIG. 2, a schematic view of an application scenario according to an exemplary embodiment is shown. As illustrated, a user is using a medical measuring device 200 and a digital video camcorder 116 is configured to record, or capture one or more images of, the medical measuring device 200 during its use. In addition, the digital video camcorder 116 is also configured to record, or capture one or more images of, a user identification object (not shown) that is disposed near the medical measuring device 200. In exemplary embodiments, the computing device is configured to utilize the digital video camcorder 116 to capture information from the medical measuring device 200 and to transmit the captured information to a cloud-enabled personal health record database 210 via a network 120.

Figure 3:
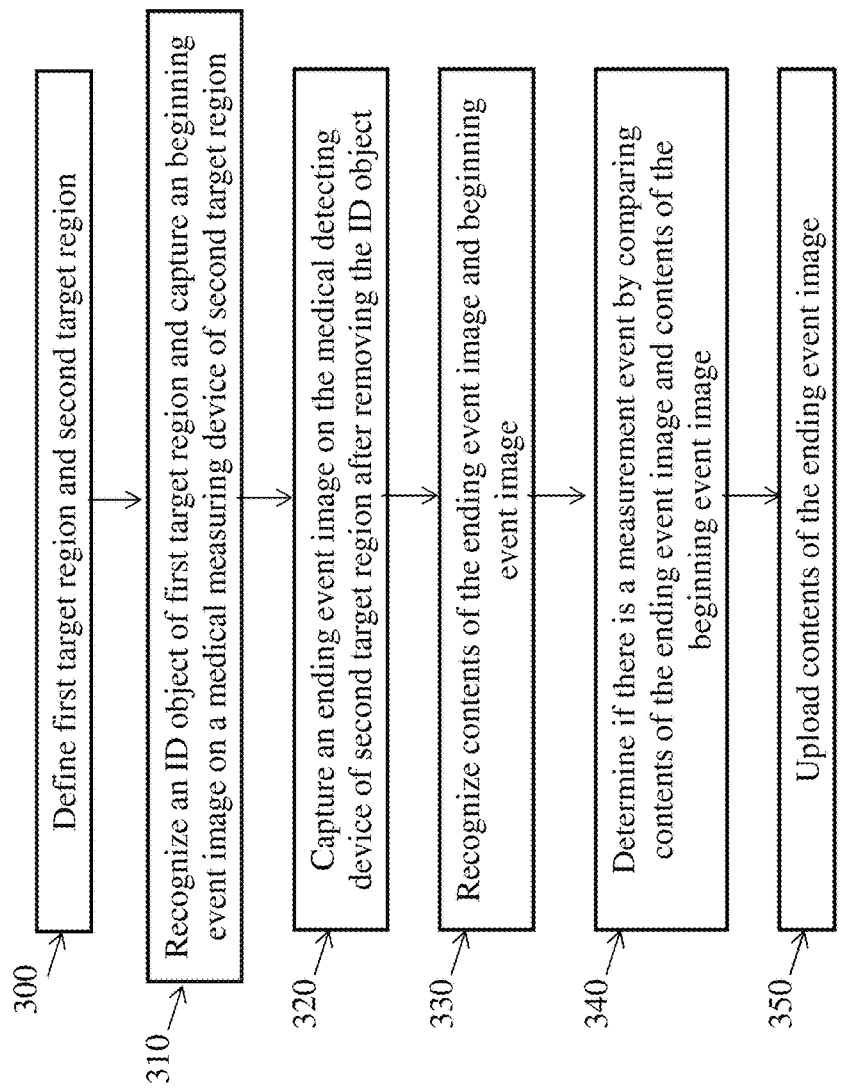
FIG. 3 is a flow chart illustrating a method for automatically uploading measurement data of a non-connected medical measuring device according to an exemplary embodiment.

Referring now to FIG. 3 a flow chart illustrating a method for automatically uploading measurement data of a non-connected medical measuring device according to an embodiment is shown. As shown at block 300, the method includes a user defining two target regions (a first target region and a second target region) on image captured by the digital video camcorder 116. The target regions are the areas of the captured image that include information to be extracted. Referring to FIG. 1, the user may define the target regions using the screen 102 of the computer device 10. For example, the user may define the target regions on the image captured by the digital video camcorder 116 as shown on the screen 102. In exemplary embodiments, the first target region may be defined on the screen 102 as a first display region 112 and the second target region may be defined on the screen 102 as a second display region 114.

Continuing with reference to FIG. 3, as shown at block 310, the method includes capturing an image of an identification object positioned in a first target region and a beginning event image of a medical measuring device positioned in a second target region. In exemplary embodiments, the computer system is configured to obtain user identification information from identification object positioned in the first target region. The identification object may be any physical object for identifying a subject (i.e., a person under test) solely, such as a work badge, a driver's license, or the like. In exemplary embodiments, the identification object can serve as a key whereby an automatic trigger records a measurement result and uploads an event.

As shown at block 320, the method also includes capturing an ending event image of the medical measuring device in the second target region after removing the identification object. Next, as shown at block 330, the method includes recognizing and retrieving measurement data of the ending event image and the beginning event image. In exemplary embodiments, the output from a medical measuring device can be either numeric (for example, the output from a body weight meter or a blood glucose meter) and/or graphic (for example, the output from an electrocardiography) and the computing device is configured to extract the output of the medical measuring device from the captured images. As shown at block 340, the method also includes determining if there is a measurement event by comparing the measurement data extracted from the ending event image and the measurement data extracted from the beginning event image.

In exemplary embodiments, a determination can be made that no measurement event exists if the numerals attributed to the ending event image and the beginning event image are identical. Likewise, a determination can be made that a measurement event does exist if the numerals attributed to the ending event image and the beginning event image are different. In other embodiments, a determination regarding the existence of a measurement event can be made based on whether the ending event image is identical to the beginning event image, rather than according to whether their measurement data are identical.

Continuing with reference to FIG. 3, as shown at block 350, upon determination that a measurement event exists, the method includes uploading the measurement data of the ending event image along with the identification data to a cloud-enabled personal health record database.

Figure 4:
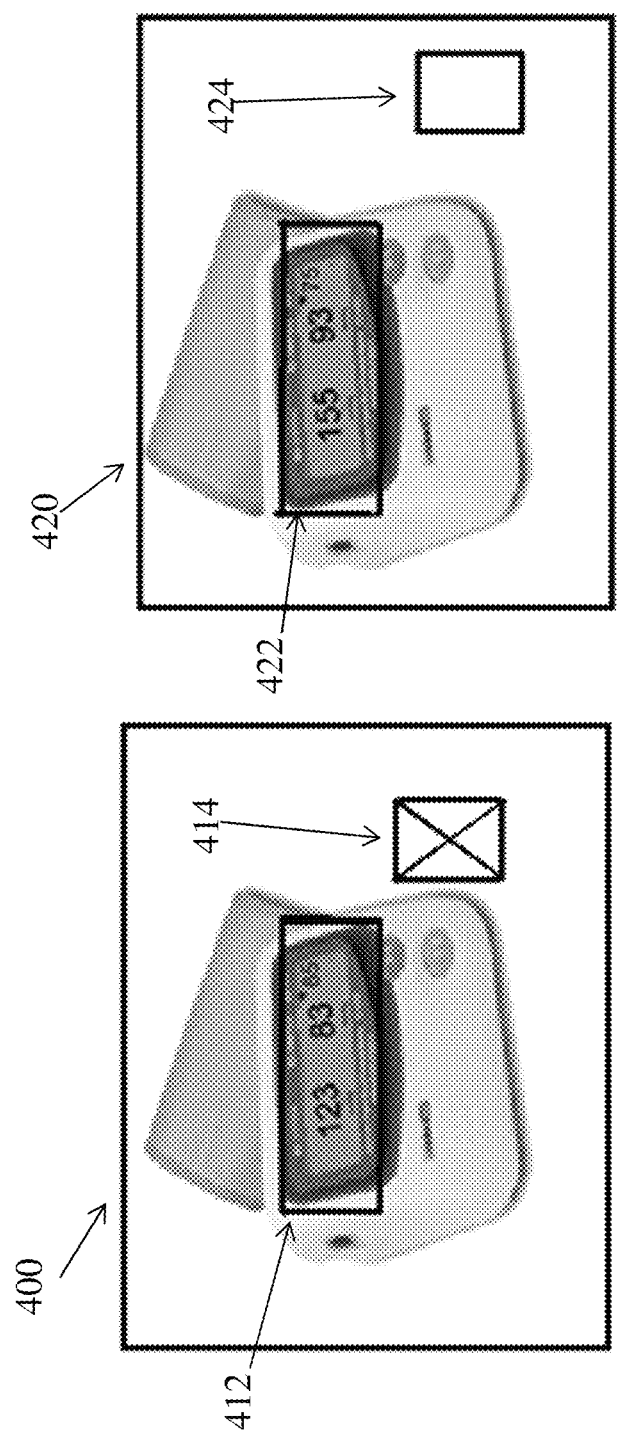
FIG. 4 is a schematic view of determining if there is a measurement event according to an exemplary embodiment.

Referring now to FIG. 4, a schematic view of determining if there is a measurement event according to an exemplary embodiment is shown. As illustrated, at a first time a display portion of a medical measuring device is located at a first display region 412 of a display 400 and an identification object is located at a second display region 414 of a display 400. At a second time, the display portion of a medical measuring device is still located at a first display region 422 of a display 420 but the identification object is not located at a second display region 424 of a display 420. Accordingly, the display portion of a medical measuring device shown in first display region 412 of a display 400 is referred to as the beginning event image and the display portion of a medical measuring device shown in first display region 422 of a display 420 is referred to as the ending event image. In exemplary embodiments, the removal of the identification object from the second display region 414 may trigger the capture of the ending event image.

In exemplary embodiments, if the information extracted from the display portion of the medical measuring device in the ending event image and information extracted from the display portion of the medical measuring device in the beginning event image are identical, it indicates that no measurement event exists. Otherwise, an measurement event exists. In response to determining that a measurement event exists, the computing device is configured to transmit the information extracted from the display portion of the medical measuring device in the ending event image to a enabled personal health record database via a network.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiments were chosen and described in order to best explain the principles of the disclosure and the practical application, and to enable others of ordinary skill in the art to understand the disclosure for various embodiments with various modifications as are suited to the particular use contemplated.

Further, as will be appreciated by one skilled in the art, aspects of the present disclosure may be embodied as a system, method, or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A method for detecting and uploading measurement data of a non-connected electrocardiograph, the method comprising:

receiving, by a processor of a computer, a video comprising an image of a display of the electrocardiograph and an image of an identifying badge from a digital video camcorder, wherein the electrocardiograph is not in electronic communication with the computer and the digital video camcorder;

displaying, by the processor, the video on a display of the computer;

receiving, by the processor, a definition of a first target region and a second target region on the display of the computer from a user, wherein the first target region corresponds to a location of the electrocardiograph on the display of the computer and the second target region corresponds to a location of the identifying badge on the display of the computer;

capturing, by the processor, from the video, an image of the identifying badge corresponding to the user, and a beginning event image of the display of the electrocardiograph, wherein the beginning event image comprises a first image of the display of the electrocardiograph prior to taking a measurement of the user;

extracting, by the processor, identification data from the image of the identifying badge;

capturing from the video, by the processor, responsive to detecting, via the processor, that the identifying badge has been removed, an ending event image of the display of the electrocardiograph, wherein the ending event image comprises a second image of the display of the electrocardiograph;

determining, by the processor, if a measurement event has occurred by comparing the ending event image of the display of electrocardiograph and the beginning event image of the electrocardiograph; and extracting, by the processor, responsive to determining that the measurement event occurred, measurement data from the ending event image of the display of electrocardiograph and uploading the measurement data to a personal health record database;

wherein the image of the identifying badge, the beginning event image, and the ending event image are captured by the digital video camcorder that is physically separate from and not in electronic communication with the non-connected electrocardiograph.

2. The method of claim 1, wherein comparing the ending event image and the beginning event image comprises comparing extracted measurement data from the ending event image and extracted measurement data from the beginning event image.

3. The method of claim 1, further comprising uploading the identification data to a personal health record database in response determining that the measurement event occurred.

4. The method of claim 1, wherein the personal health record database is a cloud based database accessed via an Internet connection.

5. A computer system for detecting and uploading measurement data of a non-connected electrocardiograph, the computer system comprising:

a digital video camcorder for capturing images comprising an image of a display of the electrocardiograph and an image of an identifying badge, wherein the electrocardiograph is not in electronic communication with the computer system;

a memory device, the memory device having computer readable computer instructions; and a processor for executing the computer readable instructions, the instructions including:

defining a first target region and a second target region on a display of the digital video camcorder, wherein the first target region corresponds to a location of the electrocardiograph on the display of the computer system and the second target region corresponds to a location of the identifying badge on the display of the computer system;

capturing an image of the identifying badge corresponding to a user, and a beginning event image of the display of the electrocardiograph, wherein the beginning event image is a first image of the display of the electrocardiograph prior to taking a measurement of the user;

extracting identification data from the image of the identifying badge;

based on detecting that the identifying badge has been removed, capturing an ending event image of the display of the electrocardiograph, wherein the ending event image is a second image of the display of the electrocardiograph;

determining if a measurement event has occurred by comparing the ending event image of the display of electrocardiograph and the beginning event image of the display of electrocardiograph; and based on determining that the measurement event occurred, extracting measurement data from the display of electrocardiograph of the ending event image and uploading the measurement data to a personal health record database.

6. The computer system of claim 5, wherein the digital video camcorder is built into the computer device.

7. The computer system of claim 5, wherein comparing the ending event image and the beginning event image comprises comparing extracted measurement data from the ending event image and extracted measurement data from the beginning event image.

8. The computer system of claim 5, wherein the instructions further include uploading the identification data to a personal health record database in response determining that the measurement event occurred.

9. A computer program product for detecting and uploading measurement data of a non-connected electrocardiograph, the computer program product comprising:

a non-transitory computer readable storage medium having program code embodied therewith, the program code executable by a processor of a computer to:

receive a video from a digital video camcorder comprising an image of a display of the electrocardiograph and an image of an identifying badge, wherein the electrocardiograph is not in electronic communication with the computer and the digital video camcorder;

display the video on a display of the computer;

receive a definition of a first target region and a second target region on the display, wherein the first target region corresponds to a location of the electrocardiograph and the second target region corresponds to a location of the identifying badge;

capture an image of the identifying badge corresponding to a user, and a beginning event image of the display of the electrocardiograph, wherein the beginning event image is a first image of the display of the medical measuring device prior to taking a measurement of the user;

extract identification data from the image of the identifying badge;

based on detecting that the identifying badge has been removed, capture an ending event image of the display of the electrocardiograph, wherein the ending event image is a second image of the display of the electrocardiograph;

determine if a measurement event has occurred by comparing the ending event image of the display of electrocardiograph and the beginning event image of the display of electrocardiograph; and based on determining that the measurement event occurred, extract measurement data from the ending event image of the display of the electrocardiograph and upload the measurement data to a personal health record database.

10. The computer program product of claim 9, wherein comparing the ending event image and the beginning event image comprises comparing extracted measurement data from the ending event image and extracted measurement data from the beginning event image.

11. The computer program product of claim 9, wherein the program code executable by the processor is further configured to define upload the identification data to a personal health record database in response determining that the measurement event occurred.

12. The computer program product of claim 9, wherein the personal health record database is a cloud based database accessed via an Internet.

* * * * *